United States Patent [19]

Bock et al.

[11] Patent Number: 4,559,338

[45] Date of Patent: Dec. 17, 1985

[54] SOLUBLE QUINAZOLINO-1,4-BENZODIAZEPIN-5,13-DIONE DERIVATIVES

[75] Inventors: Mark G. Bock; Roger M. Freidinger, both of Hatfield; Ben E. Evans, Lansdale, all of Pa.

[73] Assignee: Merck & Co., Inc., Rahway, N.J.

[21] Appl. No.: 695,117

[22] Filed: Jan. 25, 1985

[51] Int. Cl.[4] .................... C07D 403/14; A61K 31/55
[52] U.S. Cl. .............................. 514/219; 260/239.3 P
[58] Field of Search ................ 260/239.3 P; 424/251; 514/219

[56] References Cited

U.S. PATENT DOCUMENTS 3,651,046 3/1972 Derieg et al. ................ 260/239.3 P
4,187,306 2/1980 Mayer et al. ................ 260/239.3 P

*Primary Examiner*—Robert T. Bond
*Attorney, Agent, or Firm*—Richard A. Elder; Daniel T. Szura; Hesna J. Pfeiffer

[57] ABSTRACT

Novel quinazolino-1,4-benzodiazepin-5,13-dione derivatives, which are soluble in aqueous media and which have been found to be antagonists of the function of cholecystokinins (CCK), to the preparation of these compounds from compounds prepared by aerobic fermentation of certain *Aspergillus alliaceus* strains, and to the use of these compounds to antagonize the function of CCK, which antagonism is useful, e.g., for the treatment and prevention of disorders of the gastrointestinal, central nervous and appetite-regulatory systems of mammals, especially of humans.

18 Claims, No Drawings

SOLUBLE QUINAZOLINO-1,4-BENZODIAZEPIN-5,13-DIONE DERIVATIVES

The present invention is directed to novel quinazolino-1,4-benzodiazepin-5,13-dione derivatives, which are soluble in aqueous media and which have been found to be antagonists of the function of cholecystokinins (CCK), to the preparation of these compounds, and to the use of these compounds to antagonize the function of CCK, which antagonism is useful, e.g., for the treatment and prevention of disorders of the gastrointestinal, central nervous and appetite regulatory systems of mammals, especially of humans.

BACKGROUND OF THE INVENTION

Cholecystokinins (CCK) are neuropeptides (see, Mutt and Jorpes, *Biochem. J.*, 125, 678 (1971)) which exist in both gastrointestinal tissue and the central nervous system (V. Mutt, *Gastrointestinal Hormones*, G. B. J. Glass, ed., Raven Press, N.Y., 1980, p. 169), and include, e.g., CCK-33, a neuropeptide of thirty-three aminoacids and its carboxylterminal octapeptide, CCK-8. These molecules are believed to be physiological satiety hormones and, therefore, may play an important role in appetite regulation (G. P. Smith, *Eating and Its Disorders*, A. J. Stunkard and E. Stellar, Eds., Raven Press, New York, 1984, p. 67).

In addition, CCK's stimulate colonic motility, gall bladder contraction, and pancreatic enzyme secretion, and inhibit gastric emptying. CCK's reportedly also co-exist with dopamine in certain mid-brain neurons, and thus may additionally play a role in the functioning of dopaminergic systems in the brain, as well as serve as neurotransmitters in their own right. See: A. J. Prange et al., "Peptides in the Central Nervous System", *Ann. Repts. Med. Chem.*, 17, 31, 33 (1982), and references cited therein; J. A. Williams, *Biomed. Res.*, 3, 107 (1982); and J. E. Morley, *Life Sci.*, 30, 479 (1982).

Antagonists to CCK have been useful for preventing or treating CCK-related disorders of the gastrointestinal, central nervous and appetite-regulatory systems of mammals, especially of humans. Three distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G161 (1982) and P. Robberecht et al., *Mol. Pharmacol.*, 17, 268 (1980)). The second class comprises peptide antagonists which are C-terminal fragments and analogs of CCK, of which both shorter (Boc-Met-Asp-Phe-NH$_2$, Met-Asp-Phe-NH$_2$) and longer (Cbz-Tyr(SO$_3$H)-Met-Gly-Trp-Met-Asp-NH$_2$) C-terminal fragments of CCK can function as CCK-antagonists, according to recent structure-function studies (see, R. T. Jensen et al., *Biochim. Biophys. Acta.*, 757, 250 (1983), and M. Spanarkel et al., *J. Biol. Chem.*, 258, 6746 (1983)). Then, the third class of CCK receptor antagonists comprises the amino acid derivatives: proglumide, a derivative of glutaramic acid, and the N-acyl tryptophans, including para-chlorobenzoyl-L-tryptophan (benzotript), (see, W. F. Hahne et al., *Proc. Natl. Acad. Sci. U.S.A.*, 78, 6304 (1981) and R. T. Jensen et al., *Biochim. Biophys. Acta.*, 761, 269 (1983)). All of these compounds, however, are relatively weak antagonists of CCK (IC$_{50}$: generally $10^{-4}$M, but down to $10^{-6}$M in the case of the peptides) and the peptide CCK-antagonists have substantial stability and absorption problems.

The compound, 7β-((2,3,9,9Aα-tetrahydro-9α-hydroxy-2-(2-methylpropyl)-3-oxo-1H-imidazo-(1,2-A)-indol-9-yl)-methyl)quinazolino(3,2-A)(1,4) benzodiazepin-5,13-(6H,7H)dione of the formula (I):

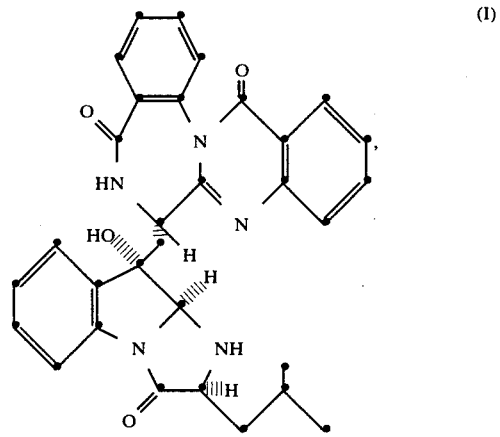

which is produced in a controlled aerobic fermentation of a strain of *Aspergillus alliaceus* Thom and Church, preferably strain ATCC No. 20655 or strain ATCC No. 20656, as disclosed in U.S. application, Ser. No. 509,883, filed Sept. 20, 1983, now U.S. Pat. No. 4,530,790 (which is incorporated herein by reference), has been shown to be a CCK-antagonist. This compound is, however, only slightly soluble in water, thus making the preparation of certain pharmaceutical formulations, such as i.v. preparations, difficult to achieve.

It was, therefore, an object of this invention to identify substances which are soluble in aqueous media and which effectively antagonize the function of cholecystokinins in disease states in mammals, especially in humans. It was another object of this invention to develop a method of preparing these novel cholecystokinin-antagonists. It was also an object of this invention to develop a method of antagonizing the function of cholecystokinins in disease states in mammals. It was still a further object of this invention to develop a method of preventing or treating disorders of the gastrointestinal, central nervous and appetite regulatory systems of mammals, especially of humans.

SUMMARY OF THE INVENTION

The instant invention is directed to certain quinazolino-1,4-benzodizepine-5,13-dione derivatives, which are soluble in aqueous media and which have been found to be antagonists of the function of cholecystokinins (CCK), to the preparation of these compounds from compounds prepared by aerobic fermentation of certain *Aspergillus alliaceus* strains, and to the use of these compounds in the treatment and prevention of disorders of the gastrointestinal, central nervous and appetite regulatory systems of mammals, especially of humans.

DETAILED DESCRIPTION OF THE INVENTION

The soluble quinazolino-1,4-benzodiazepine-5,13-dione derivatives of this invention are compounds of the formula (II):

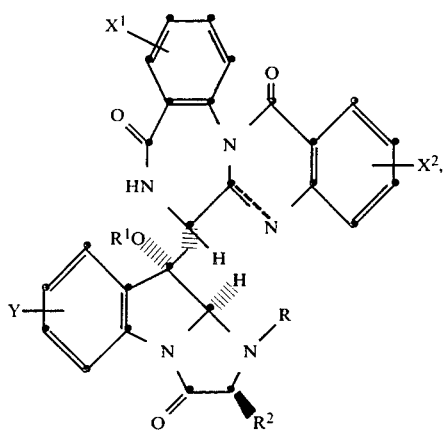

(II)

wherein:

$X^1$ and $X^2$ are independently H, Br, Cl, F, OH, O—C$_1$-C$_4$-alkyl or C$_1$-C$_4$-alkyl;

Y is H, Br, Cl, F, OH or OCH$_3$;

R is H, (CH$_2$)$_n$COOH,

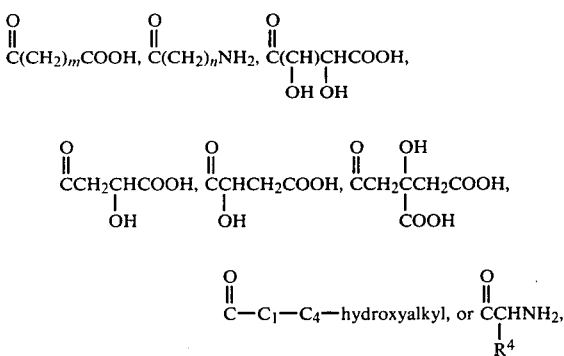

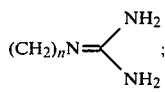

where n is 1 to 4, m is 0 to 4 and $R^4$ is H, CH$_2$OH, CHOHCH$_3$, CH$_2$-phenyl-OH, CH$_2$-phenyl-OSO$_3$H, CH$_2$-phenyl-OPO$_3$H, CH$_2$COOH, (CH$_2$)$_2$COOH, (CH$_2$)$_n$NH$_2$ or $$(CH_2)_n N = \begin{array}{c} NH_2 \\ NH_2 \end{array} ;$$

$R^1$ is R, such that if R is H, then $R^1$ is not H, and if R is not H, then $R^1$ is H;

$R^2$ is H, C$_1$-C$_4$-straight- or branched-chain alkyl, including methyl, ethyl, propyl, isopropyl, butyl, isobutyl and t-butyl; CH$_2$R$^5$, where R$^5$=hydroxy-C$_1$-C$_4$-alkyl or CH$_2$SCH$_3$; or CH$_2$-unsubstituted or monosubstituted phenyl, where the substituent is OH or OSO$_3$H; and is a variable (saturated [single] or unsaturated [double]) bond, or pharmaceutically-acceptable salts of these compounds.

Preferred compounds of formula II, according to the instant invention, include those in which

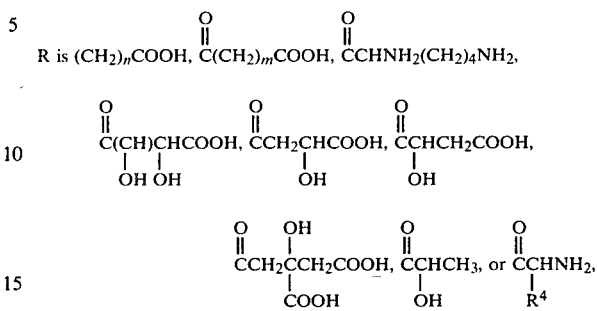

where $R^4$ is as defined above, $R^1$ is H; $R^2$ is CH$_2$CH(CH$_3$)$_2$; $X^1$, $X^2$, and Y are H, and the variable bond is saturated, and pharmaceutically-acceptable salts thereof.

Particularly preferred compounds according to the instant invention include those wherein $X^1$, $X^2$ and Y are H, R is CH$_2$COOH or $$\overset{O}{\underset{\|}{C}}(CH_2)_2COOH;$$

$R^1$ is H; $R^2$ is CH$_2$CH(CH$_3$)$_2$; and the variable bond is saturated, and pharmaceutically-acceptable salts thereof. These compounds include, particularly, 7β-[(1-carboxymethyl-2,3,9,9Aα-tetrahydro-9α-hydroxy-2-(2-methylpropyl)-3-oxo-1H-imidazo-(1,2-A)indol-9-yl)methyl]-6,7,7A-8-tetrahydro-5H,13H-quinazolino(3,2-A)-1,4-benzodiazepin-5H,13-dione sodium salt and sodium 9-(5,6,7,7A,8,13-hexahydro-5,13-dioxoquinazolino-(3,2-A)-1,4-benzodiazepin-7-yl)-2,3,9,9A-tetrahydro-9α-hydroxy-2-(2-methylpropyl)-γ,3-dioxo-1H-imidazo-(1,2-A) indole-1-butanoate.

The pharmaceutically-acceptable salts of the compounds of the instant invention include the conventional soluble, non-toxic salts or the quaternary ammonium salts of the compounds of this invention formed, for example, from non-toxic inorganic or organic acids. Such conventional non-toxic salts include those derived from inorganic acids, such as hydrochloric, hydrobromic, sulfuric, sulfamic, phosphoric, nitric and the like; or the salts derived from inorganic bases such as lithium hydroxide, sodium hydroxide, potassium hydroxide, calcium hydroxide, magnesium hydroxide, and the like; or the salts prepared from organic amines, such as trimethyl, triethyl amines and the like, or organic acids, such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Compounds according to formula II of the instant invention and salts thereof may be produced by either of two schemes, viz:

SCHEME 1
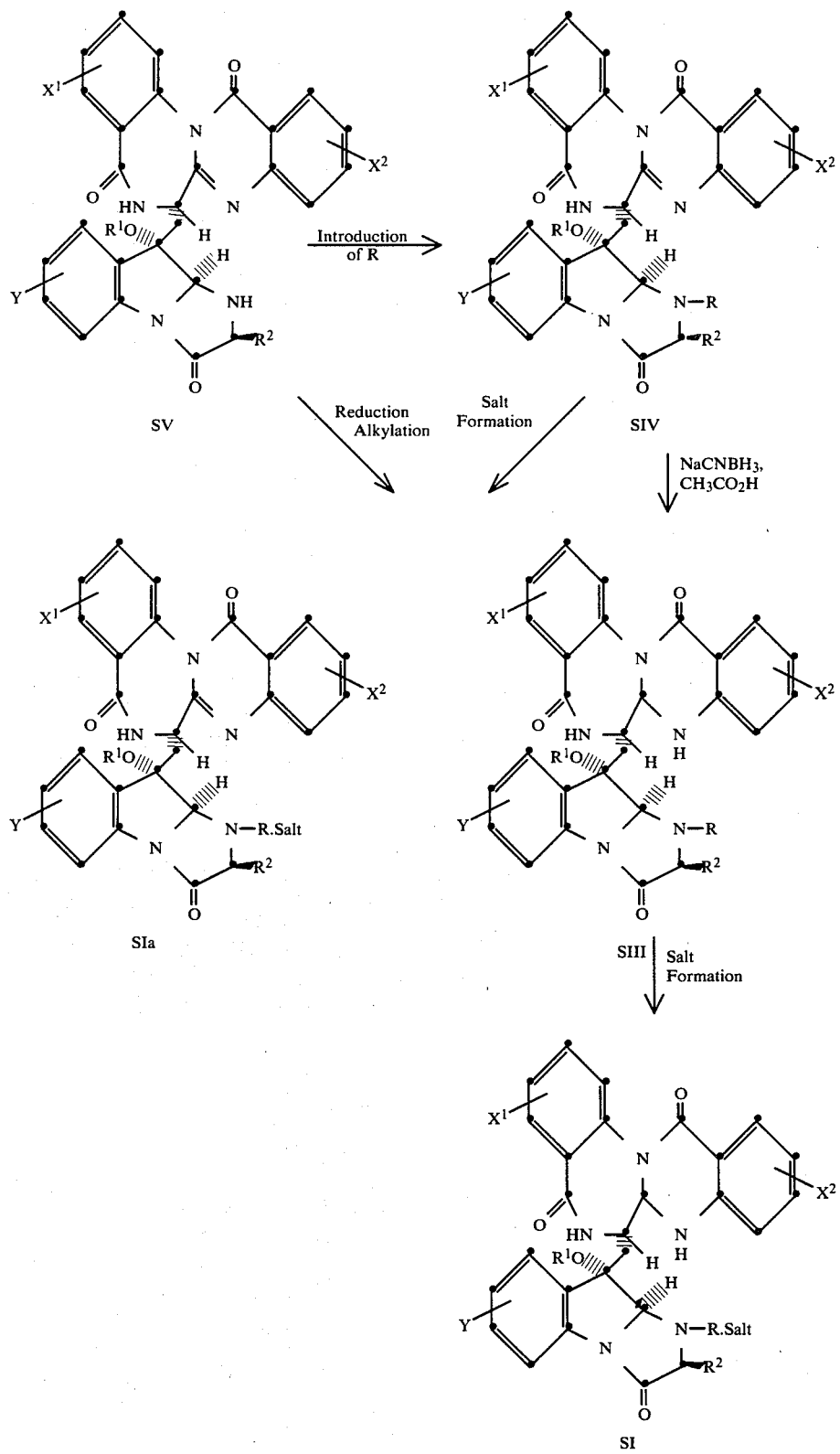
or

SCHEME 2
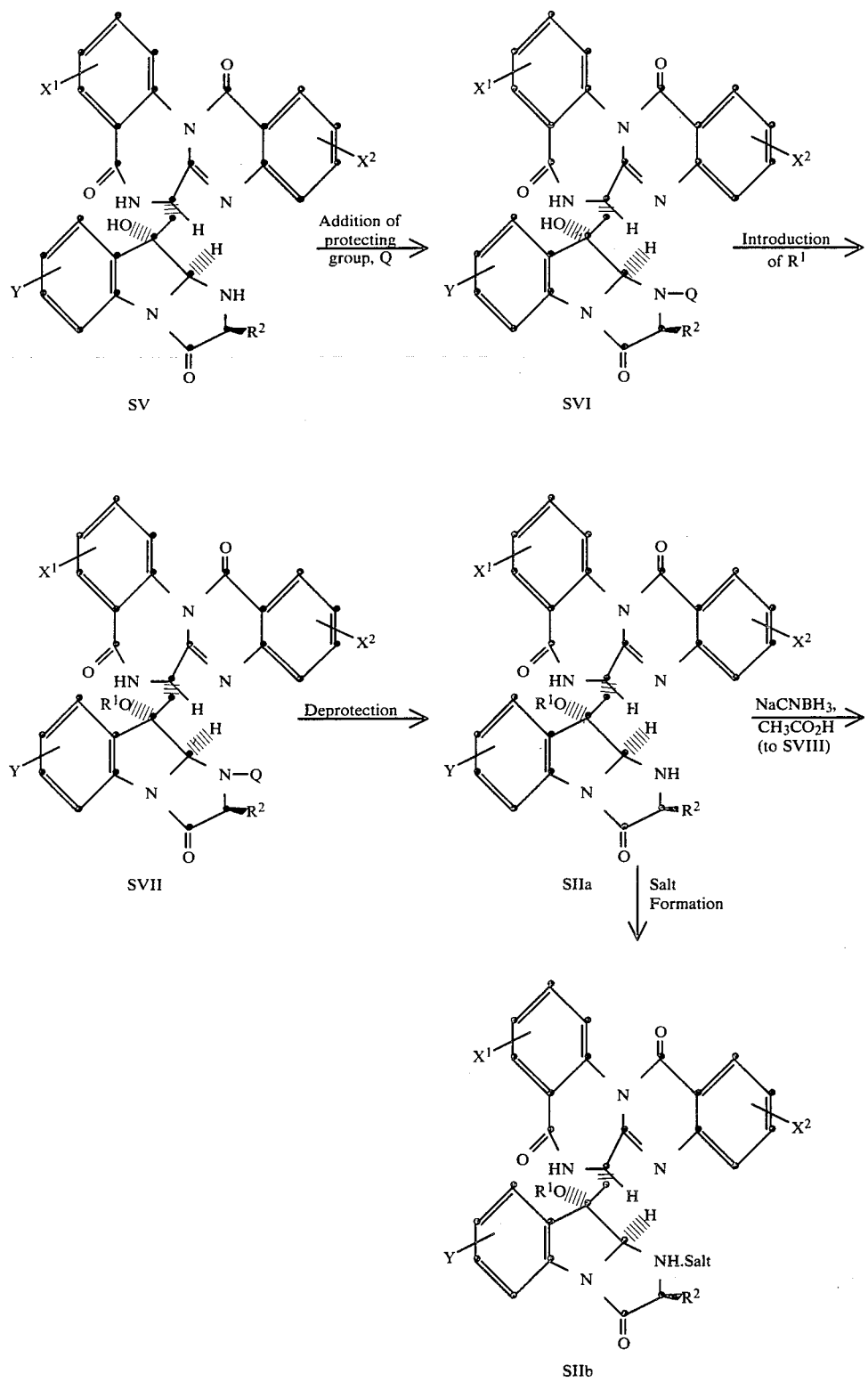

SCHEME 2
-continued

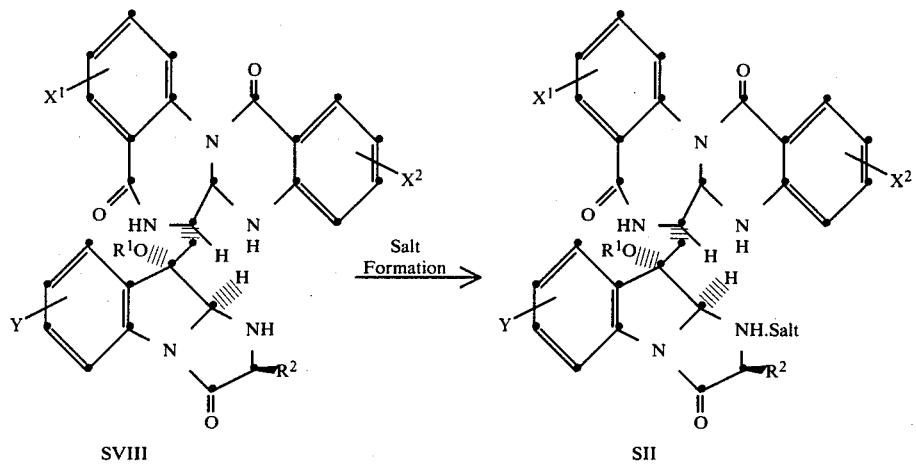

According to Scheme I, 1-substituted-imidazoindol-9-yl-5H,13H-quinazolino-1,4-benzodiazepine derivatives of the general formula SIV are prepared by acylating or alkylating an amino compound of formula SV or an acid addition salt thereof with a carbonic acid, such as succinic acid; reactive carbonic acid derivative, such as succinic anhydride; aldehyde, such as glyoxylic acid; alkyl halide or other suitable electrophilic agent. (The preparation of the imidazoindol-9-yl-5H,13H-quinazolino-1,4-benzodiazepine derivatives, SV, which are used as starting materials in the present invention, may be carried out in a known manner according to the processes described in U.S. application Ser. Nos. 509,883 and 695,113 [filed concurrently herewith.])

The acylation is carried out in an aprotic solvent at temperatures between −30° C. and the boiling point of the solvent under normal atmospheric pressure with the exclusion of moisture. If a carbonic acid anhydride or a carbonic acid halogenate is used as acylating agent, the reaction is preferably carried out in the presence of an acid binding agent such as a tertiary amine, including triethylamine, pyridine, 4-dimethylaminopyridine and the like, or an alkali metal hydroxide or alkali metal carbonate, including sodium hydroxide, potassium carbonate, and the like. Examples of suitable inert solvents include N,N-dimethylformamide, chloroform, methylene chloride, tetrahydrofuran, dioxane, toluene, and chlorobenzene.

The compounds of formula SIV may also be prepared by reacting a compound of formula SV with a carbonic acid in an inert solvent at temperatures of from −30° C. to the boiling point of the solvent, preferably at room temperature, in the presence of a suitable coupling reagent, like dicyclohexylcarbodiimide, 1-ethyl-3-(3-dimethylaminopropyl)carbodiimide hydrochloride, carbonyldiimidazole, or the like.

Additionally, compounds of formula SV may be reacted with a suitable alkyl halide, alkyl phenyl sulfonate, alkyl trifluoromethyl sulfonate, or the like, in an inert solvent in the presence of a suitable base, such as triethylamine, diisopropylethylamine, pyridine, 4-dimethylaminopyridine, sodium hydroxide, potassium carbonate, and the like, to give compounds of the general formula SIV. These reactions may be carried out at temperatures from −30° C. to the boiling point of the solvent, preferably at room temperature, for from 1 to 48 hours.

Compounds of formula SIII are obtained by dissolving compounds of the general formula SV in an acidic medium, such as acetic, trifluoroacetic or formic acids at temperatures of from −10° C. to the boiling point of the acidic medium, followed by the addition of a carboxylic aldehyde, such as glyoxylic acid, malonic acid aldehyde of succinic acid aldehyde, and a reducing agent, such as sodium, lithium or potassium borohydride, but preferably sodium cyanoborohydride, for from 30 minutes to 10 hours, preferably for 2 hours.

Compounds of the general formula SIV may then subsequently be converted to their corresponding salts of formula SIa. This may be accomplished by convention chemical means by suspending compounds of formula SIV in a solvent, such as water, methanol, ethanol, ethyl acetate, tetrahydrofuran, or other suitable organic solvent or combinations of solvents, and treating the resulting reaction mixture with stoichiometric amounts of or with an excess of the desired salt-forming inorganic or organic acid or base according to whether the compound of formula SIV contains basic or acid moieties. Examples of appropriate salt-forming inorganic bases include alkali or alkaline earth metal hydroxides, such as sodium, lithium, potassium, calcium or magnesium hydroxides, or potassium carbonate, while appropriate organic bases include tertiary amines, such as triethylamine, dibenzylethylenediamine, diisopropylethylamine, piperidine, pyrrolidine, benzylamine, α-methylbenzylamine, and the like, when R contains acidic functionality. Examples of appropriate inorganic acids for conversion of the compounds of formula SIV to the corresponding salts include mineral acids, such as hydrochloric and hydrobromic acids, while appropriate organic acids include acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like, in the cases when R contains basic functionality.

Compounds of the general formula SIII may be obtained by reducing compounds of the general formula SIV by reacting a compound of formula SIV in a protic solvent, such as water, methanol, ethanol and the like, or in an aprotic solvent, like tetrahydrofuran, with a reducing agent, such as lithium, sodium, or potassium borohydride at from $-40°$ C. to the boiling point of the solvent, for from 5 minutes to 10 hours. Preferably, the reaction is carried out in acetic acid or trifluoroacetic acid at 15° C. for 0.5 hours with sodium cyanoborohydride.

Finally, pharmaceutically-acceptable salts of the compounds according to the instant invention which have general formula SI may be synthesized from compounds of the general formula SIII using methodology described for the preparation of formula SIa compounds.

According to Scheme 2, 1-substituted-imidazoindol-9-yl-5H,13H-quinazolino-1,4-benzodiazepine derivatives of the general formula SII are prepared in a five step sequence, beginning with the selective protection of reactive functionality in compounds of general formula SV. The secondary amine in SV is protected with any of the common nitrogen-protecting groups (Q), like tert-butyloxycarbonyl or benzyloxycarbonyl, using methodology and procedures that are well-established in the art, to give compounds of the general formula SVI. The tertiary hydroxyl group in SVI may then be acylated (using the method described above for the preparation of compounds of the general formula SIV in Scheme I) or alkylated with a carbonic acid, reactive carbonic acid derivative, alkyl halide, or other suitable electrophilic agent.

Compounds of the general formula SVII are subsequently deprotected to give compounds of the general formula SIIa. The method of deprotecting the secondary nitrogen group will depend on the choice of protecting group, but follows the procedures that are well-established in the art.

Preparation of salts of SIIa compounds may be accomplished following the procedure outlined in Scheme I above for conversion of SIV products.

Preparation of compounds of formula SVIII may be accomplished following the procedure for synthesis of compounds of formula SIII above.

Preparation of pharmaceutically-acceptable salts of compound according to the instant invention which have formula SII may then be accomplished following the description for salt formation from Scheme I above.

Chiral acylating and alkylating agents of both configurations may be used for the production of analogs of the compounds according to the instant invention. The preferred stereochemical configuration of the products according to the instant invention are those defined in Formula II.

Screening of the novel compounds according to the present invention to determine biological activity and obtain an $IC_{50}$ value for them, in order to identify significant CCK-antagonism, may be accomplished using an $^{125}I$-CCK receptor binding assay and in vitro isolated tissue preparations. These tests involve the following:

CCK receptor binding (pancreas) method

CCK-33 is radiolabeled with $^{125}I$-Bolton Hunter reagent (2000 Ci/mmole), as described by Sankara et al. (*J. Biol. Chem.*, 254, 9349–9351, 1979). Receptor binding is performed according to Innis and Snyder (*Proc. Natl. Acad. Sci.*, 77, 6917–6921, 1980), with the minor modification of adding the additional protease inhibitors, phenyl-methane sulfonyl fluoride and o-phenanthroline, which have no effect on the $^{125}I$-CCK receptor binding assay.

The whole pancreas of a male Sprague-Dawley rat (200–350 g), which has been sacrificed by decapitation, is dissected free of fat tissue and homogenized in 20 volumes of ice-cold 50 mM Tris HCl (pH 7.7 at 25° C.) with a Brinkman Polytron PT-10. The homogenates are centrifuged at 48,000 g for 10 minutes, then the resulting pellets are resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 μl of buffer (for total binding), or unlabeled CCK-8 sulfate sufficient to give a final concentration of 1 μM of CCK-8 (for nonspecific binding), or the compounds of the formula of the compounds according to the instant invention (for determination of antagonism to $^{125}I$-CCK binding) and 25 μl of $^{125}I$-CCK-33 (30,000–40,000 cpm), are added to 450 μl of the membrane suspensions in microfuge tubes. All assays are run in duplicate or triplicate, and the reaction mixtures are incubated at 37° C. for 30 minutes and centrifuged in a Beckman Microfuge (4 minutes) immediately after adding 1 ml of ice-cold incubation buffer. The supernatant is aspirated and discarded, and the pellets are counted with a Beckman Gamma 5000. For Scatchard analysis to determine the mechanism of inhibition of $^{125}I$-CCK binding by the most potent compounds (*Ann. N.Y. Acad. Sci.*, 51, 660, 1949), $^{125}I$-CCK-33 is progressively diluted with increasing concentrations of CCK-33.

CCK receptor binding (brain) method

CCK-33 is radiolabeled and the binding is performed according to the description for the pancreas method, with modifications according to Saito et al., *J. Neurochem.*, 37, 483–490, 1981.

Male Hartley guinea pigs (300–500 g) are sacrificed by decapitation, and the brains are removed and placed in ice-cold 50 mM Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkman polytron PT-10. The homogenates are centrifuged at 42,000 g for 15 minutes, then the resulting pellets are resuspended in 80 volumes of binding assay buffer (10 mM N-2-hydroxy-ethylpiperazine-N'-2-ethanesulfonic acid (HEPES), 5 mM $MgCl_2$, 1 mM ethylene glycol-bis-(β-amino-ethylether-N,N'-tetraacetic acid (EGTA), 0.4% BSA and 0.25 mg/ml bacitracin, pH 6.5).

The remainder of the binding assay method is as described for the pancreas method, except that the reaction mixtures are incubated at 25° C. for 2 hours before centrifugation.

An additional method of confirming competitive antagonism of CCK which may be used is the following:

Isolated guinea pig gall bladder method

The two halves of the gall bladders, free of adjacent tissue, of male Hartley guinea pigs (400–600 g), which have been sacrificed by decapitation, are suspended under 1 g tension along the axis of the bile duct in 5 ml organ bath, containing a Kreb's bicarbonate solution of 118 mM NaCl, 4.75 mM KCl, 2.54 mM $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues are washed every 10 minutes for 1 hour to obtain equilibrium prior to the beginning of the study and the isometric contractions of the strips are recorded using Statham (60 g: 0.12 mm) strain gauges and a Hewlett-Packard 77588 recorder.

CCK-8 is added cumulatively to the baths and $EC_{50}$'s are determined using regression analysis. After washout (every 10 minutes for 1 hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal contractile response, indicates competitive antagonism of CCK from this method.

The ability of the compounds of the instant invention to antagonize CCK makes these compounds useful as pharmaceutical agents for mammals, especially for humans, for the treatment and prevention of disorders wherein CCK may be involved. Examples of such disease states include gastrointestinal disorders, especially such as irritable bowel syndrome or ulcers, excess pancreatic or gastric secretion, acute pancreatis, or motility disorders; central nervous system disorders, caused by CCK interactions with dopamine, such as neuroleptic disorders, tardive dyskineasia, Parkinson's disease, psychosis or Gilles de la Tourette Syndrome; and disorders of appetite regulatory systems.

The compounds of the instant invention or pharmaceutically-acceptable salts thereof, may be administered to a human subject either alone or, preferably, in combination with pharmaceutically-acceptable carriers or diluents, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist of CCK in a human subject, the daily dosage will normally be determined by the prescribing physician. Moreover, the dosage will vary according to the age, weight, and response of the individual patient, as well as the severity of the patient's symptoms. In most instances, an effective daily dosage will be in the range of from about 1 mg to about 1500 mg, and preferably, of from 10 mg to about 500 mg administered in single or divided doses. In some cases, however, it may be necessary to use dosages outside these limits.

The invention is further defined by reference to the following examples which are intended to be illustrative and not limiting.

EXAMPLE 1

Preparation of 2,3,9,9Aα-tetrahydro-9α-hydroxy-2-(2-methylpropyl)-γ,3-dioxo-9-(5,6,7,13-tetrahydro-5,13-dioxoquinazolino(3,2-A)-1,4-benzodiazepin-7-yl)-1H-imidazo(1,2-A)indole-1-butanoic acid To a solution of 7β-((2,3,9,9Aα-tetrahydro-9α-hydroxy-2-(2-methylpropyl)-3-oxo-1H-imidazo(1,2-A)indol-9-yl)methyl)quinazolino(3,2-A)benzodiazepine-5,13-(6H,7H)-dione (1.34 g, 2.5 mmole) in 25 ml of dry methylene chloride was added succinic anhydride (1.25 g, 12.5 mmole) and 4-dimethylaminopyridine (305 mg, 2.5 mmole). The reaction mixture was protected from moisture (calcium chloride) and stirred at room temperature for 20 hours. The reaction mixture was diluted to five times the original volume with methylene chloride, then washed with 10% citric acid solution and brine. The organic phase was dried (sodium sulfate) and concentrated to give 2.4 g of crude product as a foam. The crude reaction product was purified by flash chromatography on silica gel (chloroform-methanol-acetic acid elution, 95:4:1) to yield 678 mg of the analytically-pure material; m.p. 200° C. (d).

$R_f$=0.29 (93:6:1 chloroform-methanol-acetic acid).

FAB Mass Spec: (M++H) 636.

Pmr (Methanol-$d_4$): 1.03 (3H, d), 1.12 (3H, d), 2.02 (1H, m), 2.15 (1H, m), 2.57 (1H, m), 2.35 (2H, m), 2.7 (3H, m), 2.85 (1H, m), 3.3 (2H, m), 4.45 (1H, m), 4.9 (1H, m), 6.1 (1H, s), 6.78 (1H, dxd), 6.92 (2H, p), 7.27 (1H, d), 7.48 (2H, m), 7.7 (3H, m), 7.95 (1H, d), 8.1 (1H, d, NH exchanged).

Elemental Anal: Calc. for $C_{35}H_{33}N_5O_7 \cdot C_2H_9O_2$: N, 10.07; C, 63.88; H, 5.36. Found: N, 10.26; C, 63.86; H, 5.01.

EXAMPLE 2

Preparation of sodium 2,3,9,9Aα-tetrahydro-9α-hydroxy-2-(2-methylpropyl)-γ,3-dioxo-9-(5,6,7,13-tetrahydro-5,13-dioxoquinazolino(3,2-A)-1,4-benzodiazepin-7-yl)-1H-imidazo(1,2-A)indole-1-butanoate To a suspension of the acid of Example 1 (150 mg, 0.24 mmole) in 1 ml of water was added, at room temperature, 2.4 ml of 0.1 molar sodium hydroxide solution (0.24 mmole). The reaction mixture became homogeneous within 20 minutes, the water was evaporated under reduced pressure, and the resulting residue was dried in vacuo at 120°/0.5 Torr for 18 hours.

Pmr ($D_2O$): 0.9 (6H, m, methyls), 4.3 (1H, m, α proton), 4.73 (1H, m, α proton in quinazoline ring).

Elemental Anal: Calc. for $C_{35}H_{32}N_5O_7Na3H_2O$: N, 9.84; C, 59.06; H, 5.38. Found: N, 10.00; C, 59.34; H, 5.29.

EXAMPLE 3

Preparation of
1,2,9,9Aα-tetrahydro-9α-hydroxy-1-(2,6-diaminophenoyl)-2-(2-methylpropyl)-9-[(5,6,7,13-tetrahydro-5,13-dioxoquinazolino(3,2-A)-1,4-benzodiazepin-7-yl)methyl]-3H-imidazo(1,2-A)indol-3-one dihydrochloride 7β-((2,3,9,9Aα-Tetrahydro-9α-hydroxy-2-(2-methylpropyl)-3-oxo-1H-imidazo(1,2-A)indol-9-yl)methyl)-quinazolino(3,2-A)benzodiazepine-5,13-(6H,7H)dione (1.07 g, 2 mmole), N$^\alpha$-t-Boc-N-Cbz-L-lysine anhydride (12.29 g, 16.6 mmole), and 4-dimethylaminopyridine (732 mg, 6 mmole) were reacted in 30 ml of dry methylene chloride at room temperature. The reaction was complete after 2 hours, at which time it was diluted with 600 ml of ethyl acetate and washed in succession with 10% citric acid solution (2×100 ml), 50% sodium bicarbonate solution (3×100 ml), and brine. The organic phase was dried with magnesium sulfate and concentrated to give 11.74 g of crude material, which was applied directly to a silica gel column using chloroform-ethanol (95:5) as eluant. The fractions 12 to 18 (50 ml each) were combined, concentrated and re-chromatographed with ethyl acetate-hexane (70:30) to give 1.35 g of homogeneous product, the N$^\alpha$-t-Boc-N$^\epsilon$-Cbz-protected intermediate for the production of the indol-3-one dihydrochloride:

$R_f$=0.37 (5% ethanol/chloroform).

FAB Mass Spec: (M+ +H) 899.

Elemental Anal: Calc. for $C_{50}H_{55}N_7O_9.3/4H_2O$: N, 10.77; C, 65.98; H, 6.28. Found: N, 10.38; C, 66.00; H, 6.40.

The product so obtained was converted to the indol-3-one dihydrochloride by dissolving 800 mg of the chromatographically-homogeneous intermediate in 40 ml of ethanol/50% aqueous acetic acid (4:1 v/v), treated with 300 mg of 10% palladium-on-carbon catalyst and hydrogenated in a Parr apparatus at 48 psi for 2½ hours. The reaction mixture was filtered through Celite and the solvent was removed under reduced pressure, with the residual oil being chromatographed on silica gel using chloroform-ethanol-ammonia (80:10:1) as eluant, where after forty 20 ml fractions, the gradient was changed to 80:20:2. The product was contained in fractions 51-66 and the solvent was removed under reduced pressure, with the residual oil (625 mg) being dissolved in ethyl acetate. The resulting solution was cooled to 0° C. and treated with a continuous stream of hydrogen chloride gas for 1 hour and the excess reagent and solvent were roto-evaporated to give a water-soluble white powder (m.p. 120° C. (d)).

EXAMPLE 4

Preparation of
9-(5,6,7,7A,8,13-hexahydro-5,13-dioxoquinazolino(3,2-A)-1,4-benzodiazepin-7-yl)-2,3,9,9A-tetrahydro-9α-hydroxy-2-(2-methylpropyl)-γ,3-dioxo-1H-imidazo(1,2-A)indole-1-butanoic acid dihydrate To 1.5 ml of glacial acetic acid was added the acid of Example 1 (160 mg, 0.25 mmole) and the reaction mixture was cooled to 15° C. The reaction mixture was treated in one portion with 64 mg (1.0 mmole) of sodium cyanoborohydride and stirred for 30 minutes, then poured into 40 ml of water. The resulting suspension was extracted with ethyl acetate (3×40 ml) and the combined organic extracts were washed with brine. Roto-evaporation of the dried (magnesium sulfate) extracts afforded 250 mg of a glassy oil and trituration with ether gave 112 mg of a white powder:

m.p. 211° C.;

$R_f$=0.3 (CHCl$_3$—CH$_3$OH—CH$_3$CO$_2$H, 92:7:1);

FAB Mass Spec: (M+ +H) 638, (M+ +Na) 660.

Pmr (CDCl$_3$/Methanol-d$_4$): 1.0 (6H, m), 1.57 (1H, m), 1.8 (1H, m), 2.0 (1H, m), 2.15 (1H, m), 2.7 (2H, m), 2.8 (1H, m), 2.95 (1H, m), 3.3 (1H, m), 3.55 (2H, m), 4.67 (1H, dxd), 4.95 (1H, d), 5.79 (1H, s), 5.92 (1H, s), 6.93 (1H, dxd), 7.0 (1H, m), 7.17 (1H, dxd), 7.3 (1H, m), 7.39 (1H, m), 7.46 (1H, d), 7.5 (2H, m), 7.55 (1H, m), 7.83 (1H, d), 7.87 (1H, d);

Elemental Anal: Calc. for $C_{35}H_{35}N_5O_7.2H_2O$: N, 10.40; C, 62.39; H, 5.83. Found: N, 10.93; C, 62.36; H, 5.87.

EXAMPLE 5

Preparation of sodium
9-(5,6,7,7A,8,13-hexahydro-5,13-dioxoquinazolino(3,2-A)-1,4-benzodiazepin-7-yl)2,3,9,9A-tetrahydro-9α-hydroxy-2-(2-methylpropyl)-γ,3-dioxo-1H-imidazo(1,2-A)indole-1-butanoate trihydrate A 0.05 molar solution of sodium hydroxide (1.8 ml) was added to 57 mg of acid of Example 4 (0.09 mmole) and after stirring for 15 minutes at room temperature, the homogeneous reaction mixture was concentrated to yield 50 mg of a white solid:

m.p. 240° C.;

FAB Mass Spec: (M+ +H) 660, (M+ +Na) 682.

Pmr (D$_2$O): according to theory.

Elemental Anal: Calc. for $C_{35}H_{34}N_5O_7Na \cdot 3H_2O$: N, 9.81; C, 58.90; H, 5.65. Found: N, 10.32; C, 58.95; H, 5.57.

EXAMPLE 6

Preparation of
1,2,9,9Aα-tetrahydro-9α-hydroxy-1-[2-amino-5-((-phenylmethoxy)carbonyl)aminopentanoyl]-2-(2-methylpropyl)-9-[(5,6,7,13-tetrahydro-5,13-dioxoquinazolino(3,2-A)-1,4-benzodiazepin-7-yl)methyl]-3H-imidazo(1,2-A)indol-3-one hydrochloride 7β-((2,3,9,9Aα-Tetrahydro-9α-hydroxy-2-(2-methylpropyl)-3-oxo-1H-imidazo(1,2-A)indol-9-yl)methyl)-quinazolino(3,2-A)benzodiazepine-5,13-(6H,7H)-dione (535 mg, 1 mmole), N$^\alpha$-t-Boc-N$^\delta$-Cbz-L-ornithine anhydride (3.57 g, 5 mmole), and 4-dimethylamino pyridine (122 mg, 1 mmole) were mixed at room temperature and stirred in 15 ml of dry methylene chloride. The resulting reaction mixture was protected from moisture and stirred for 24 hours, whereupon 5 mmole more of the anhydride and 1 mmole more of 4-dimethylaminopyridine was added to the reaction mixture. After a total of 36 hours, the reaction mixture was diluted with 250 ml of ethyl acetate and washed, in succession, with 5% citric acid solution (2×50 ml), 50% aqueous sodium bicarbonate (2×50 ml) and brine. The organic phase was dried (MgSO$_4$) and concentrated to yield 3.8 g of a solid (foam). Chromatography of this crude product on silica gel using initially ethyl acetate-hexane (60:40 v/v), then ethyl acetate-hexane (70:30 v/v) afforded 482 mg of pure N$^\alpha$-t-Boc-protected intermediate for the production of the indol-3-one hydrochloride:

$R_f$=0.57; m.p. 79°-89° C.; FAB Mass Spec: (M+ +H) 885.

This intermediate (200 mg) was dissolved in 20 ml of dry ethyl acetate and treated at 0° C. with a continuous stream of hydrogen chloride gas for 60 minutes. The solvent and excess HCl gas were removed under reduced pressure and the residue was purified by preparative thick layer chromatography using chloroform-ethanol-ammonia (90:7:0.5) as eluant. In this way, 121 mg of the title compound was obtained in pure form:

m.p. 123° C. (soften);

FAB Mass Spec: (M+ −HCl) 784.

Pmr (Methanol-$d_4$): 1.0 (6H, 2d), 1.3 (2H, t), 1.6 (2H, m), 1.82 (1H, m), 1.9 (2H, m), 2.48 (1H, dxd), 3.10 (1H, dxd), 3.17 (1H, dxt), 4.04 (1H, t), 4.28 (2H, m), 4.47 (2H, m), 5.05 (2H, m), 5.55 (1H, s), 7.02 (1H, t), 7.09 (1H, t), 7.16 (1H, t), 7.34 (5H, m), 7.39 (1H, d), 7.55 (1H, t), 7.65 (2H, m), 7.67 (1H, d), 7.77 (1H, t), 7.81 (1H, t), 7.9 (1H, d), 7.99 (1H, d).

EXAMPLE 7

Preparation of
7β-[(1-carboxymethyl-2,3,9,9Aα-tetrahydro-9α-hydroxy-2-(2-methylpropyl)-3-oxo-1H-imidazo(1,2-A)indol-9-yl)methyl]-6,7,7A-8-tetrahydro-5H,13H-quinazolino(3,2-A)-1,4-benzodiazepin-5H,13-dione solvate 7β-[(2,3,9,9Aα-Tetrahydro-9α-hydroxy-2-(2-methylpropyl)-3-oxo-1H-imidazo(1,2-A)indol-9-yl)methyl]-quinazolino(3,2-A)-1,4-benzodiazepin-5,13-(6H,7H)-dione (1.07 g, 2 mmole) was dissolved in 20 ml of glacial acetic acid and, in succession, glyoxylic acid (0.252 g, 6 mmole) and sodium cyanoborohydride (1.257 g, 20 mmole) were added to this solution at room temperature under nitrogen. The reaction was terminated after two hours (TLC monitoring) by the addition of 150 ml of water and the resulting white precipitate was collected, washed with water and then purified via flash chromatography on silica gel [95:5 v/v chloroform-methanol (400 ml), 90:10 v/v chloroform-methanol (225 ml), 80:20 v/v chloroform-methanol (150 ml) and 75:25 v/v chloroform-methanol (675 ml)] to yield the analytical product, 194 mg.

$R_f$=0.3 chloroform-methanol 4:1 v/v; 99% pure by HPLC.

Pmr (360 MHz, Methanol-$d_4$): 0.875 (3H, d), 0.925 (3H, d), 1.3 (1H, m), 1.45 (1H, m), 1.85 (1H, m), 2.13 (1H, dxd), 2.3 (1H, dxd), 3.37 (2H, d), 3.6 (1H, m), 4.2 (1H, t), 5.29 (1H, d), 5.36 (1H, d), 6.85 (1H, t), 7.0 (1H, d), 7.1 (1H, t), 7.3 (4H, m), 7.55 (4H, m), 7.8 (1H, d).

Elemental Anal: Calc. for $C_{33}H_{33}N_5O_6 \cdot 0.75CHCl_3$: N, 10.22; C, 59.16; H, 4.97. Found: N, 10.19; C, 59.05; H, 5.14.

EXAMPLE 8

Preparation of
7β-[(1-carboxymethyl-2,3,9,9Aα-tetrahydro-9α-hydroxy-2-(2-methylpropyl)-3-oxo-1H-imidazo(1,2-A)indol-9-yl)methyl]-6,7,7A-8-tetrahydro-5H,13H-quinazolino(3,2-A)-1,4-benzodiazepin-5H,13-dione sodium salt solvate 7-[(1-Carboxymethyl-2,3,9,9Aα-tetrahydro-9α-hydroxy-2-(2-methylpropyl)-3-oxo-1H-imidazo(1,2-A)indol-9-yl)methyl]-6,7,7A,8-tetrahydro-5H,13H-quinazolino(3,2-A)-1,4-benzodiazepine-5H,13-dione solvate (148 mg, 0.21 mmole) was dissolved in 5 ml of dry methanol and treated with 2.16 ml of a 0.1 N sodium hydroxide solution. Roto-evaporation of the solvent under reduced pressure afforded the sodium salt which was dried initially at 65° C. for 20 hours, then at 109° C. for 24 hours.

Elemental Anal: Calc. for $C_{33}H_{32}N_5O_6Na \cdot 3.38H_2O \cdot 0.75CHCl_3$ N, 9.12; C, 52.77; H, 5.18. Found: N, 8.82; C, 52.62; H, 4.88.

EXAMPLE 9

Preparation of
7β-[(2,3,9,9Aα-tetrahydro-9α-(3-carboxy-1-oxopropoxy)-2-(2-methylpropyl)-3-oxo-1H-imidazo(1,2-A)indol-9-yl)methyl]quinazolino(3,2-A)-1,4-benzodiazepin-5,13-(6H,7H)-dione monohydrate 7β-((2,3,9,9Aα-Tetrahydro-9α-hydroxy-2-(2-methylpropyl)-3-oxo-1H-imidazo(1,2-A)indol-9-yl)methyl)-quinazolino(3,2-A)benzodiazepine-5,13(6H,7H)-dione (1.0 g, 1.87 mmole) and 4-dimethylaminopyridine (228 mg, 1.87 mmole) were suspended in 20 ml of dry methylene chloride and stirred at 0° C. The reaction mixture was then treated with benzylchloroformate (1.5 ml, 9.35 mmole) and allowed to warm to room temperature over 15 minutes. Nine more equivalents of benzylchloroformate and 1 equivalent of base were added and the reaction was allowed to stir at room temperature for 6 hours. Four hundred milliliters of methylene chloride were added and the organic phase was washed with 10% citric acid solution (2×50 ml) and brine. The dried (MgSO₄) extracts were roto-evaporated to give an oil (3 g) which was purified by silica gel chromatography (4% ethanol/chloroform); $R_f$=0.33; 360 MHz Pmr according to theory; FAB Mass Spec: (M+ +H) 670.

This purified material (the N-Cbz-derivative of Example 1) (1.53 g, 2.3 mmole) was then subjected to further acylation at the tertiary hydroxyl group using the monobenzyl ester of succinic acid (718 mg, 3.45 mmole), 4-dimethylaminopyridine (421 mg, 3.45 mmole) and dicyclohexylcarbodiimide (3.45 ml of a 1M solution in methylene chloride) in 15 ml of methylene chloride. After overnight stirring, the reaction mixture was diluted with methylene chloride (250 ml), filtered, and the filtrate washed with 2×50 ml of 5% citric acid solution, 50% sodium bicarbonate solution (2×50 ml), and brine. Evaporation of the solvent lead to 1.69 g of an amorphous solid: m.p. 79°–89° C. (soften & gas evolution).

300 mg of this product was dissolved in 75 ml of absolute ethanol, treated with 50 mg of 10% palladium-on-carbon and hydrogenated on a Parr apparatus at 50 psi for 4½ hours. Solvent and catalyst were removed to give 170 mg of an oil which was purified by preparative thick layer chromatography (90:10 chloroform/ethanol) to yield the title compound as an off-white solid:

ir (CDCl₃, partial): 1700, 1610, 1605, 1480, 1380, 1250 cm$^{-1}$.

FAB Mass Spec: (M+ +H) 636.

Pmr (Methanol-$d_4$): 0.85 (3H, d), 0.90 (3H, d), 1.15 (1H, m), 1.51 (1H, m), 1.67 (1H, m), 2.47 (1H, dxd), 2.56 (2H, bd), 2.6 (2H, bd), 3.6 (1H, dxd), 4.1 (1H, m), 4.4 (1H, dxd), 5.62 (1H, d), 7.09 (1H, dxt), 7.26 (1H, dxt), 7.33 (2H, t), 7.55 (2H, m), 7.60 (1H, dxt), 7.67 (1H, m), 7.72 (2H, m), 7.83 (1H, m), 8.20 (1H, m).

EXAMPLE 10

Solubility and Activity Testing

The compounds of Examples 1–9 were tested for solubility in deionized water and pH 7.4 phosphate buffer and as CCK-antagonists (pancreas assay) with the following results:

| Compound from Example | X¹ | X² | Y | Substituents R | R¹ | R² | 7A-8 Bond | Solubility[1] | Anti-CCK Activity[2] IC$_{50}$ (μM) |
|---|---|---|---|---|---|---|---|---|---|
| 1 | H | H | H | —C(=O)(CH₂)₂CO₂H | H | CH₂CH(CH₃)₂ | Unsaturated | 9.5 (pH 7.4 Buffer) 0.28 (H₂O) | 230 |
| 2 | H | H | H | —C(=O)(CH₂)₂CO₂Na | H | CH₂CH(CH₃)₂ | Unsaturated | 72 (H₂O) | 27 |
| 3 | H | H | H | —CCH(NH₂)(CH₂)₄NH₂·HCl | H | CH₂CH(CH₃)₂ | Unsaturated | — | 3.8 |
| 4 | H | H | H | —C(=O)(CH₂)₂CO₂H | H | CH₂CH(CH₃)₂ | Saturated | 10.8 (pH 7.4 Buffer) 0.54 (H₂O) | 6.1 |
| 5 | H | H | H | —C(=O)(CH₂)₂CO₂Na | H | CH₂CH(CH₃)₂ | Saturated | >8.9 (H₂O) | 1.7 |
| 6 | H | H | H | —CCH(NH₂)(CH₂)₃NHCbz·HCl | H | CH₂CH(CH₃)₂ | Unsaturated | 0.24 (H₂O) | 1.8 |
| 7 | H | H | H | —CH₂CO₂H | H | CH₂CH(CH₃)₂ | Saturated | 10.5 (H₂O) | 1.4 |
| 8 | H | H | H | —CH₂CO₂Na | H | CH₂CH(CH₃)₂ | Saturated | >5.2 (H₂O) | 0.8 |
| 9 | H | H | H | H | —C(=O)(CH₂)₂—CO₂H | CH₂CH(CH₃)₂ | Unsaturated | — | 85 |

[1]Solubilities in mg/ml.
[2]I-CCK-8 Pancreas assay.

What is claimed is:

1. Quinazolino-1,4-benzodiazepin-5,13-dione derivatives of the formula:

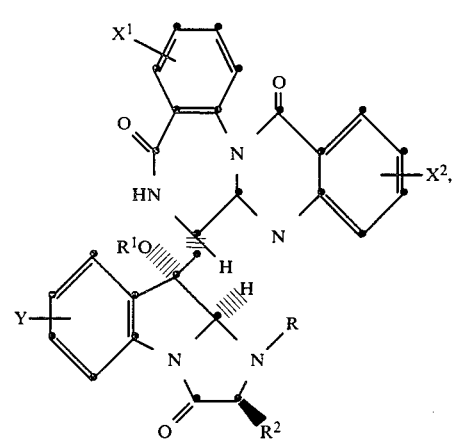

wherein:
X¹, X² and Y are independently H, Br, Cl, F, OH, O—C₁-C₄-alkyl or C₁-C₄-alkyl;
R is H, (CH₂)$_n$COOH,

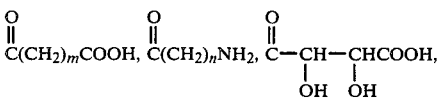

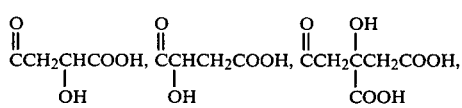

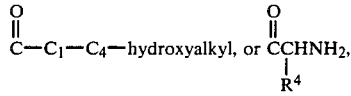

where n is 1 to 4, m is 0 to 4 and R⁴ is H, CH₂OH, CHOHCH₃, CH₂-phenyl-OH, CH₂-phenyl-OSO₃H, CH₂-phenyl-OPO₃H, CH₂COOH, (CH₂)₂COOH, (CH₂)$_n$NH₂ or

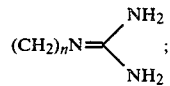

R¹ is R, such that if R is H, then R¹ is not H, and if R is not H, then R¹ is H;
R² is H, C₁-C₄-straight- or branched-chain alkyl; CH₂R⁵, where R⁵=hydroxy-C₁-C₄-alkyl or CH₂SCH₃; or CH₂-unsubstituted or monosubstituted phenyl, where the substituent is OH or OSO₃H;
is a single or double bond,
or pharmaceutically-acceptable salts of these compounds.

2. A compound according to claim 1, wherein R is (CH₂)$_n$COOH,

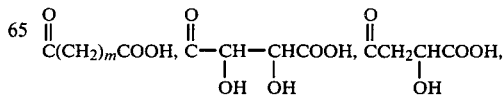

-continued

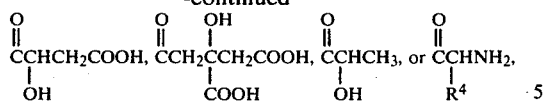

where n, m and $R^4$ are as defined in claim 1; $R^1$, $X^1$, $X^2$ and Y are H; $R^2$ is $CH_2CH(CH_3)_2$; and the ═ bond is a single bond, or pharmaceutically-acceptable salts thereof.

3. A compound according to claim 1, wherein R is $CH_2COOH$ or

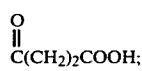

$R^1$, $X^1$, $X^2$ and Y are H; $R^2$ is $CH_2CH(CH_3)_2$; and the ═ bond is a single bond, or pharmaceutically-acceptable salts thereof.

4. A compound according to claim 1 selected from 7β-[(1-carboxymethyl-2,3,9,9Aα-tetrahydro-9α-hydroxy-2-(2-methylpropyl)-3-oxo-1H-imidazo-(1,2-A)-indol-9-yl)methyl]-6,7,7A-8-tetrahydro-5H,13H-quinazolino(3,2-A)-1,4-benzodiazepin-5H,13-dione sodium salt; sodium 9-(5,6,7,7A,8,13-hexahydro-5,13-dioxoquinazolino(3,2-A)-1,4-benzodiazepin-7-yl)-2,3,9,9A-tetrahydro-9α-hydroxy-2-(2-methylpropyl)-γ,3-dioxo-1H-imidazo(1,2-A)indole-1-butanoate; 7β-[(1-carboxymethyl-2,3,9,9Aα-tetrahydro-9α-hydroxy-2-(2-methylpropyl)-3-oxo-1H-imidazo-(1,2-A)-indol-9-yl)methyl]-6,7,7A-8-tetrahydro-5H,13H-quinazolino-(3,2-A)-1,4-benzodiazepin-5H,13-dione; 1,2,9,9Aα-tetrahydro-9α-hydroxy-1-[2-amino-5-((phenylmethoxy)carbonyl)aminopentanoyl]-2-(2-methylpropyl)-9-[(5,6,7,13-tetrahydro-5,13-dioxoquinazolino-(3,2-A)-1,4-benzodiazepin-7-yl)methyl]-3H-imidazo-(1,2-A)indol-3-one hydrochloride; 9-(5,6,7,7A,8,13-hexahydro-5,13-dioxoquinazolino(3,2-A)-1,4-benzodiazepin-7-yl)-2,3,9,9A-tetrahydro-9α-hydroxy-2-(2-methylpropyl)-γ,3-dioxo-1H-imidazo(1,2-A)indole-1-butanoic acid; 1,2,9,9Aα-tetrahydro-9α-hydroxy-1-(2,6-diaminohexanoyl)-2-(2-methylpropyl)-9-[(5,6,7,13-tetrahydro-5,13-dioxoquinazolino(3,2-A)-1,4-benzodiazepin-7-yl)methyl]-3H-imidazo(1,2-A)-indol-3-one dihydrochloride; sodium 2,3,9,9Aα-tetrahydro-9α-hydroxy-2-(2-methylpropyl)-γ,3-dioxo-9-(5,6,7,13-tetrahydro-5,13-dioxoquinazolino(3,2-A)-1,4-benzodiazepin-7-yl)-1H-imidazo(1,2-A)indole-1-butanoate; 7β-[(2,3,9,9Aα-tetrahydro-9α-(3-carboxy-1-oxopropoxy)-2-(2-methylpropyl)-3-oxo-1H-imidazo-(1,2-A)indol-9-yl)methyl]quinazolino(3,2-A)-1,4-benzodiazepin-5,13-(6H,7H)-dione; and 2,3,9,9Aα-tetrahydro-9α-hydroxy-2-(2-methylpropyl)-γ,3-dioxo-9-(5,6,7,13-tetrahydro-5,13-dioxoquinazolino(3,2-A)-1,4-benzodiazepin-7-yl)-1H-imidazo-(1,2-A)indole-1-butanoate acid.

5. A compound according to claim 1 selected from 7β-[(1-carboxymethyl-2,3,9,9Aα-tetrahydro-9α-hydroxy-2-(2-methylpropyl)-3-oxo-1H-imidazo-(1,2-A)-indol-9-yl)methyl]-6,7,7A-8-tetrahydro-5H,13H-quinazolino(3,2-A)-1,4-benzodiazepin-5H,13-dione sodium salt and sodium 9-(5,6,7,7A,8,13-hexahydro-5,13-dioxoquinazolino(3,2-A)-1,4-benzodiazepin-7-yl)-2,3,9,9A-tetrahydro-9α-hydroxy-2-(2-methylpropyl)-γ,3-dioxo-1H-imidazo(1,2-A)indole-1-butanoate.

6. A process for preparing quinazolino-1,4-benzodiazepin-5,13-dione derivatives of formula II:

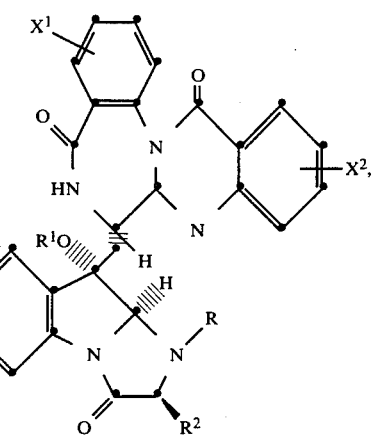

wherein:

$X^1$, $X^2$ and Y are independently H, Br, Cl, F, OH, O—$C_1$–$C_4$-alkyl or $C_1$–$C_4$-alkyl;

R is H, $(CH_2)_n$COOH,

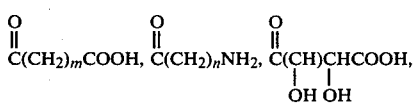

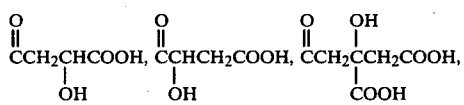

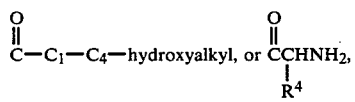

where n is 1 to 4, m is 0 to 4 and $R^4$ is H, $CH_2OH$, $CHOHCH_3$, $CH_2$-phenyl-OH, $CH_2$-phenyl-$OSO_3H$, $CH_2$-phenyl-$OPO_3H$, $CH_2COOH$, $(CH_2)_2COOH$, $(CH_2)_n NH_2$ or

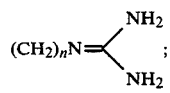

$R^1$ is R, such that if R is H, then $R^1$ is not H, and if R is not H, then $R^1$ is H;

$R^2$ is H, $C_1$–$C_4$-straight- or branched-chain alkyl; $CH_2R^5$, where $R^5$=hydroxy-$C_1$–$C_4$-alkyl or $CH_2SCH_3$; or $CH_2$-unsubstituted or monosubstituted phenyl, where the substituent is OH or $OSO_3H$; and ═ is a single or double bond bond;

comprising acylating an amino compound of formula SV:

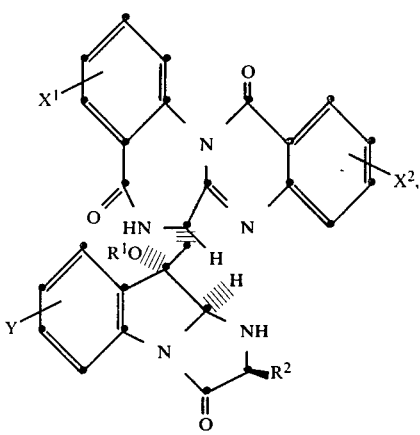

with a suitable electrophilic agent in a suitable aprotic solvent then reducing the resulting acylated amino compound in a protic or aprotic solvent with a suitable reducing agent, or comprising dissolving an amino compound of formula SV in an acidic medium, followed by the addition of a carboxylic aldehyde and a reducing agent and reaction of these components.

7. A process according to claim 6, wherein the soluble quinazolino-1,4-benzodiazepine-5,13-dione derivatives are suspended in a suitable solvent and reacted with a suitable salt-forming agent.

8. A process according to claim 6, wherein suitable electrophilic agent is succinic anhydride or glyoxylic acid; a suitable aprotic solvent is N,N-dimethyl-formamide, chloroform, methylene chloride, tetrahydrofuran, dioxane, toluene or chlorobenzene, and a suitable protic solvent is water, methanol, ethanol, acetic acid or trifluoroacetic acid; a suitable reducing agent is sodium cyanoborohydride, lithium borohydride, sodium borohydride, or potassium borohydride; a suitable acidic medium is acetic acid or trifluoroacetic acid; and the carboxylic aldehyde is glyoxylic acid, malonic acid aldehyde or succinic acid aldehyde.

9. A process according to claim 6, wherein the amino compound of formula SV is acylated at temperatures between −30° C. and the boiling point of the solvent, with the exclusion of moisture and the resulting acylated amino compound is reduced at from −40° C. to the boiling point of the protic or aprotic solvent for from 5 minutes to 10 hours, or the amino compound of formula SV is dissolved in an acidic medium at temperatures of from −10° C. to the acidic medium's boiling point and after the addition of the carboxylic aldehyde and a reducing agent, the reaction occurs over 30 minutes to 10 hours.

10. A process according to claim 7, wherein a suitable solvent is water, methanol, ethanol, ethyl acetate or tetrahydrofuran and a suitable salt-forming agent is sodium hydroxide, lithium hydroxide, potassium hydroxide, potassium carbonate, triethylamine, diisopropylethylamine when R is (CH$_2$)$_n$COOH,

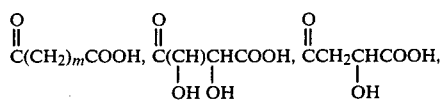

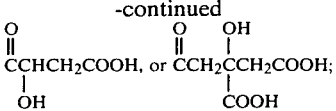

or is hydrochloric acid, hydrobromic acid, acetic acid, trifluoracetic acid, propionic acid, succinic acid, glycolic acid, stearic acid, lactic acid, isethionic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethanedisulfonic acid or oxalic acid, when R is

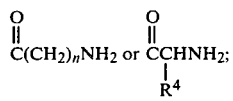

or is hydrochloric acid, hydrobromic acid, trifluoracetic acid, isethionic acid, methanesulfonic acid or ethanedisulfonic acid, when R is

wherein n, m and R$^4$ are as defined in claim 7.

11. A composition comprising a pharmaceutically-effective amount for antagonism of the function of cholecystokinins in mammals of one or more quinazolino-1,4-benzodiazepin-5,13-dione derivatives or pharmaceutically-acceptable salts of these derivatives, according to claim 1, and a pharmaceutically-acceptable carrier.

12. A composition according to claim 11, wherein the quinazolino-1,4-benzodiazepin-5,13-dione derivatives comprise one or both of 7β-[(1-carboxymethyl-2,3,9,9Aα-tetrahydro-9α-hydroxy-2-(2-methylpropyl)-3-oxo-1H-imidazo-(1,2-A)indol-9-yl)methyl]-6,7,7A-8-tetrahydro-5H,13H-quinazolino-(3,2-A)-1,4-benzodiazepin-5H,13-dione sodium salt and sodium 9-(5,6,7,7A,8,13-hexahydro-5,13-dioxoquinazolino-(3,2-A)-1,4-benzodiazepin-7-yl)-2,3,9,9A-tetrahydro-9α-hydroxy-2-(2-methylpropyl)-γ,3-dioxo-1H-imidazo-(1,2-A)indole-1-butanoate.

13. A composition according to claim 11, wherein the pharmaceutically-effective amount is from about 1 mg to about 1500 mg, administered in single or divided doses.

14. A composition according to claim 13, wherein the pharmaceutically-effective amount is from about 10 mg to about 500 mg.

15. A composition according to claim 11, wherein the mammals are humans.

16. A method of preventing or treating a mammal for disorders of the gastrointestinal, central nervous or appetite regulatory systems which comprises administering to said mammal a pharmaceutically-effective amount of one or more quinazolino-1,4-benzodiazepin-5,13-dione derivatives or pharmaceutically -acceptable salts thereof, according to claim 1.

17. A method according to claim 16, wherein a pharmaceutically-acceptable carrier is also administered.

18. A method according to claim 16 or claim 17, wherein the mammals are humans and a pharmaceutically-effective amount is from 1 mg to about 1500 mg, administered in single or divided doses.

* * * * *

UNITED STATES PATENT AND TRADEMARK OFFICE
CERTIFICATE OF CORRECTION

PATENT NO. : 4,559,338   Page 1 of 2
DATED : Dec. 17, 1985
INVENTOR(S) : Mark G. Bock; Roger M. Freidinger and Ben E. Evans It is certified that error appears in the above—identified patent and that said Letters Patent is hereby corrected as shown below:

In Claim 1, column 20, line 58

"is a single or double bond,"

should read

--- ⫽ is a single or double bond,---

In Claim 1, column 21, line 8

"and Y are H; $R^2$ is $CH_2CH(CH_3)_2$; and the    bond is a"

should read

---and Y are H; $R^2$ is $CH_2CH(CH_3)_2$; and the ⫽ bond is a---

In Claim 3, column 21, line 18

"$R^1$, $X^1$, $X^2$, and Y are H; $R^2$ is $CH_2CH(CH_3)_2$; and the"

should read

---$R^1$, $X^1$, $X^2$ and Y are H; $R^2$ is $CH_2CH(CH_3)_2$; and the ⫽ ---

In Claim 6, column 22, line 64

" ⫽ phenyl, where the substituent is OH or $OSO_3H$; and"

should read

---phenyl, where the substituent is OH or $OSO_3H$; and---

UNITED STATES PATENT AND TRADEMARK OFFICE
CERTIFICATE OF CORRECTION

PATENT NO. : 4,559,338           Page 2 of 2
DATED : Dec. 17, 1985
INVENTOR(S) : Mark G. Bock; Roger M. Freidinger and Ben E. Evans It is certified that error appears in the above—identified patent and that said Letters Patent is hereby corrected as shown below:

In Claim 6, column 22, line 65

"is a single or double bond bond"

should read

--- |: is a single or double bond; ---

Signed and Sealed this

Fifteenth Day of July 1986

[SEAL]

Attest:

Attesting Officer

DONALD J. QUIGG

Commissioner of Patents and Trademarks